United States Patent
Welter

(10) Patent No.: US 7,214,834 B2
(45) Date of Patent: May 8, 2007

(54) PROCESS FOR PREPARING ENANTIOMERICALLY PURE 1,1'-SPIROBIINDANE-6,6'-DIOL DERIVATIVES

(75) Inventor: Thomas R. Welter, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 307 days.

(21) Appl. No.: 10/895,160

(22) Filed: Jul. 20, 2004

(65) Prior Publication Data

US 2006/0020150 A1    Jan. 26, 2006

(51) Int. Cl.
*C07C 39/12* (2006.01)
(52) U.S. Cl. ...................... 568/719; 568/700
(58) Field of Classification Search ......... 568/700, 568/719
See application file for complete search history.

(56) References Cited

U.S. PATENT DOCUMENTS

| | | | |
|---|---|---|---|
| 4,701,566 A | 10/1987 | Faler et al. | |
| 4,701,567 A | 10/1987 | Tanabe et al. | |
| 4,791,234 A | 12/1988 | Faler et al. | |
| 5,856,422 A | 1/1999 | Chan et al. | |
| 6,132,641 A | 10/2000 | Rietz et al. | |
| 6,288,206 B1 | 9/2001 | Stewart et al. | |

FOREIGN PATENT DOCUMENTS

| DE | 26 45 020 | 4/1978 |
|---|---|---|
| DE | 40 27 385 A1 | 3/1991 |

OTHER PUBLICATIONS

Birman et al (Tetrahedron: Asymetry 10(1999) 125-131).*
Birman et al., 1,1'-Spirobiindane-7,7'-diol: a novel, C2-symmetric chiral ligand, Tetrahedron: Asymmetry, 10 (1999), 125-131.*
Birman, V.B. et al. "1,1'-Spirobiindane-7-7'-diol: A novel C2-symmetric chiral ligand". Tetrahedron: Asymmetry, Elsevier Science Publishers, Amsterdam, NL, Jan. 15, 1999 pp. 125-131.
Fabbri, D; Delogu, G.: Journal of Organic Chemistry, vol. 60, 1995, pp. 6599-6601, XP002355327, compounds 1B, 2B, 4B, 5B.
B. Kohler, et al., Chemistry—A European Journal, 7(14), pp. 3000-3004 (2001).
G. A. Consiglio, et al., *Journal of Supramolecular Chemistry*, 2(2002), pp. 293-300.
J. Chem. Soc., 1962, pp. 418-421.
Revista Chimie, 34, pp. 1069-1074 (1983).
J. Org. Chem., 55, pp. 4966-4969 (1990).
J. Med. Chem., 43, pp. 2031-2039 (2000).
J. Amer. Chem. Soc., 122, pp. 2053-2061 (2000).
R. J. Kazlauskas, Journal of the American Chemical Society, 111(13),pp. 4953-4959 (1989).
Bull. Soc. Chem. Japan, 44, pp. 496-505 (1971).
Pending U.S. Appl. No. 10/737,457 filed Dec. 16, 2003 entitled "Liquid-Crystal Compositions Comprising Chiral Compounds".

* cited by examiner

*Primary Examiner*—Thurman K. Page
*Assistant Examiner*—Chukwuma Nwaonicha
(74) *Attorney, Agent, or Firm*—Carl F. Ruoff; Lynne M. Blank

(57) ABSTRACT

The present invention relates to a method for the chemical separation of the enantiomers of 1,1'-spirobiindane-6,6'-diol derivatives comprising providing a racemic chiral 1,1'-spirobiindane-6,6'-diol derivative, reacting a nonracemic chiral component with the racemic chiral 1,1'-spirobiindane-6,6'-diol derivative to afford a mixture of diastereomeric diesters, separating the mixture of diastereomeric diesters to provide a substantially pure individual diastereomeric diester, and chemically removing the ester groups from the substantially pure individual diastereomeric diester to provide a nonracemic chiral 1,1'-spirobiindane-6,6'-diol derivative.

46 Claims, No Drawings

PROCESS FOR PREPARING ENANTIOMERICALLY PURE 1,1'-SPIROBIINDANE-6,6'-DIOL DERIVATIVES

FIELD OF THE INVENTION

The present invention involves the chemical separation of enantiomers of 1,1'-spirobiindane-6,6'-diol derivatives.

BACKGROUND OF THE INVENTION 1,1'-Spirobiindane-6,6'-diol derivatives of Structure I:

Structure 2

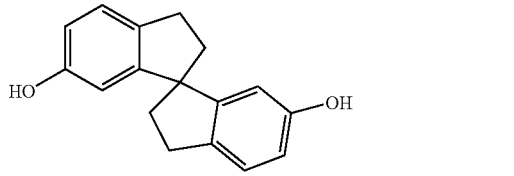

have recently found substantial utility as, among other things, precursors for chiral polymers as disclosed in U.S. Pat. Nos. 5,856,422A and 6,288,206B1, precursors for macrocyclic compounds as disclosed in B. Kohler, et al., *Chemistry—A European Journal*, 7(14), 3000 (2001), precursors for chiral cyclophanes as disclosed in G. A. Consiglio, et al., *Journal of Supramolecular Chemistry*, 2(1–3), 293 (2003), and, more recently, precursors for the preparation of novel chiral dopants for nematic liquid crystal formulations as disclosed in U.S. patent application Ser. No. 10/737,457. Many of these applications require the use of enantiomerically enriched 1,1'-spirobiindane-6,6'-diol derivatives.

Methods for the efficient, environmentally responsible, large-scale preparation of these nonracemic derivatives are limited. Many syntheses of racemic 1,1'-spirobiindane-6,6'-diol derivatives have been disclosed, for example, in U.S. Pat. Nos. 4,701,566, 4,701,567, 4,791,234A, 6,132,641A, DE2645020, DE4027385, *J. Chem. Soc.*, 1962, *Revista Chimie*, 34, 1069 (1983).418. *J. Org. Chem.*, 55, 4966 (1990), *J. Med. Chem.*, 43, 2031(2000), and *J. Amer. Chem. Soc.*, 122, 2055(2000). These methods necessarily provide a 1:1 enantiomeric mixture of the derived 1,1'-spirobiindane-6,6'-diols. While methods for separating these mixtures do exist, they have proved wanting (vide infra).

Four general methods for the isolation of nonracemic compounds are known to those skilled in the art of organic chemistry: 1) chiral synthesis of individual enantiomers, 2) chiral chromatographic separation of racemates, 3) enzymatic resolutions of racemates, and 4) use of chiral auxiliaries for diastereomeric formation eventually leading to enantiomer separation. No methods for the direct synthesis of individual 1,1'-spirobiindane-6,6'-diol enantiomers are known. Further, the separation of racemic mixtures into their constituent enantiomers via chiral chromatography is primarily an analytical technique. While such technology for the "preparative" separation of racemic mixtures does exist, it is generally limited to a maximum of several grams of material, less than needed for many commercial applications. Further, the technology for these preparative separations is limited in structural scope, not readily allowing separation of the desired 1,1'-spirobiindane-6,6'-diol derivatives.

A method for the enzymatic separation of the enantiomers of a 1,1'-spirobiindane-6,6'-diol derivatives has been reported by R. J. Kazlauskas U.S. Pat. No. 4,879,421 and *Journal of the American Chemical Society*, 111(13), 4953–9 (1989). This methodology employs (1) the preparation of achiral esters of the racemic 1,1'-spirobiindane-6,6'-diol derivatives, (2) the enantio-selective enzymatic hydrolysis of these racemic mixtures and (3) the eventual isolation of substantially enantiomerically enriched samples of the requisite 1,1'-spirobiindane-6,6'-diol derivatives after achiral chromatographic purification. While this technology has been demonstrated to be useful in the preparation of hundreds of grams of nonracemic 1,1'-spirobiindane-6,6'-diol derivatives, it suffers from substantial drawbacks. The initial step of Kazlauskas resolution requires the synthetic preparation of ester derivatives of the racemic 1,1'-spirobiindane-6,6'-diol. This material is then exposed to an appropriate enzyme formulation in aqueous media for several days. During this reaction phase, care must be taken to control reaction temperature and solution alkalinity. Careful analysis of reaction composition is also needed to alter reaction conditions, thus ensuring optimal conversion to nonracemic product. With the completion of the enzymatic reaction, multiple solvent extractions provide a nonracemic residue that must be further purified. Achiral silica gel chromatography, employing the environmentally suspect methylene chloride as an eluant, then provides the nonracemic products. Finally, saponification of residual ester groups provides the desired 1,1'-spirobiindane-6,6'-diol in good overall yield and high racemic purity. Application of this protocol to multi-kilogram production is limited, among other factors, by extended reaction times, multiple extractions leading to excessive solvent waste, large scale chromatographies, and the use of environmentally unacceptable chlorinated solvents.

Japanese chemists previously described the separation of a 1,1'-spirobiindane-6,6'-diol derivative using diastereomer formation, *Bull. Soc. Chem. Japan*, 44, 496 (1971). In that case, the requisite racemic spirobiindandiol substrate was reacted with a nonracemic chiral isocyanate to yield a mixture of diastereomeric mixture of urethane products. The mixture was then purified by repeated recrystallizations from benzene, a solvent designated a cancer suspect agent by the EPA. Finally, the desired spirobiindane was secured by chemical degradation of the chiral urethane groups.

Esters of phenols in general are very commonly encountered organic compounds. Within this context, they are meant to include structurally those derived from a 1,1'-spirobiindane-6,6'-diol and a carboxylic acid component. The acid component can be alkyl, cycloalkyl, aryl, alkyloxy (alkylcarbonic acid), cycloalkyl (cycloalkylcarbonic acid), or aryloxy (arylcarbonic acid). General methods for the preparation of phenyl esters are apparent to those skilled in the art. These method include: (1) reaction of the phenol with an acid chloride under basic conditions; (2) reaction of a phenol with a carboxylic acid under acidic conditions; (3) reaction of the phenol with a chloroformate; (4) reaction of a phenol and a carboxylic acid using a condensing agent; (5) reaction of the phenol with phosgene to prepare an intermediary phenyl chloroformate, that then can be condensed with a second phenol or alcohol, and similar transformations.

A variety of nonracemic chiral carboxylic acids, acid chlorides, chloroformates, and alcohols are available for the preparation of esters of potential use in separating 1,1'-spirobiindane-6,6'-diol enantiomers. These substrates may in turn be derived from natural sources, isolated chromatographically, prepared via enantio-selective methods, or otherwise purified. Most commonly, natural product derivatives are employed as chiral auxiliary agents.

Problem to be Solved

The known methods for separating enantiomers of 1,1'-spirobiindane-6,6'-diol necessarily require extensive chromatographies, long reaction times, and toxic solvents. For these reasons large-scale manufacturing separation of these enantiomers cannot be accomplished in an environmentally or economically acceptable way.

SUMMARY OF THE INVENTION

The present invention relates to a method for the chemical separation of the enantiomers of 1,1'-spirobiindane-6,6'-diol derivatives comprising providing a racemic chiral 1,1'-spirobiindane-6,6'-diol derivative, reacting a nonracemic chiral component with the racemic chiral 1,1'-spirobiindane-6,6'-diol derivative to afford a mixture of diastereomeric diesters, separating the mixture of diastereomeric diesters to provide a substantially pure individual diastereomeric diester, and chemically removing the ester groups from the substantially pure individual diastereomeric diester to provide a nonracemic chiral 1,1'-spirobiindane-6,6'-diol derivative.

ADVANTAGEOUS EFFECT OF THE INVENTION

The present invention includes several advantages, not all of which are incorporated in a single embodiment. This method is shown to avoid the need for long chemical reaction times, carefully controlled reaction conditions, detailed reaction analyses, chromatographic separations, and the use of chlorinated solvents. This method is a simple reaction/separation sequence affording chiral resolution of spirobiindanediols of use in preparing novel chiral dopants and other high value materials.

DETAILED DESCRIPTION OF THE INVENTION

The present invention relates to a novel method for the chemical separation of the enantiomers of 1,1'-spirobiindane-6,6'-diol derivatives. This method includes formation of chiral, nonracemic esters from the racemic 1,1'-spirobiindane-6,6'-diol derivatives, the separation of the so-derived mixture to provide nonracemic diastereomeric components, and finally, chemical removal of the appended ester groups to provide resolved enantiomerically enriched 1,1'-spirobiindane-6,6'-diol derivatives.

A variety of racemic 1,1'-spirobiindane-6,6'-diol derivatives can be obtained by means of known synthetic procedures or less likely from commercial sources. Such compounds useful in this process are generally described by compounds of Structure 2, wherein $R_1$, $R_2$, $R_3$, and $R_4$ are independently hydrogen, or any carbon substituents, X groups are independently any substituent, and n are independently an integer 0–3 and wherein these substituents may for a ring. Preferably, all of the $R_1$, $R_2$, $R_3$, and $R_4$ are hydrogen or lower alkyl group to include groups containing one to about eight carbon atoms, e.g. methyl ethyl, n-propyl, n-butyl, isobutyl, 2-pentyl, tert-pentyl and the like. It is most preferred that the $R_1$ and $R_4$ groups are hydrogen or methyl and the $R_2$ and $R_3$ groups are hydrogen and n=0.

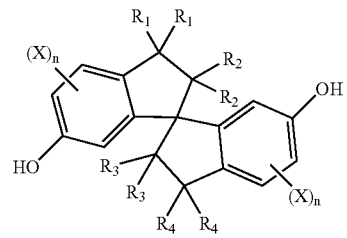

Structure 2

Representative 1,1'-spirobiindane-6,6'-diol derivatives are presented herein. These examples are meant to be instructive not limiting.

I-1
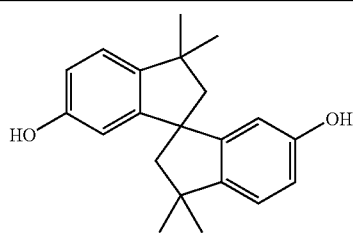

I-2
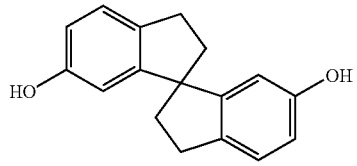

I-3
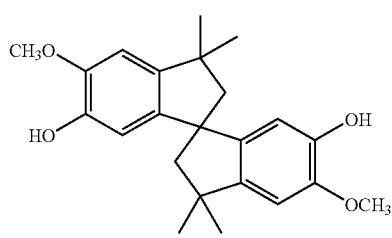

I-4
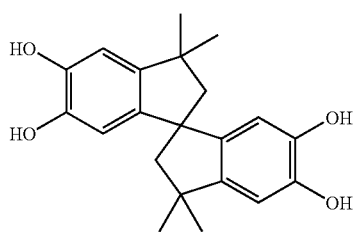

I-5
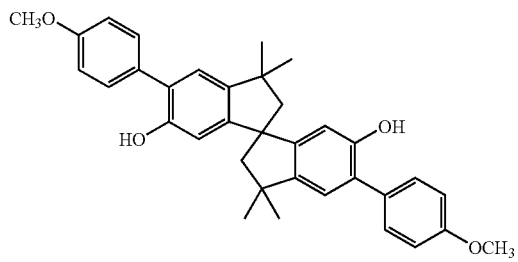

-continued

I-6
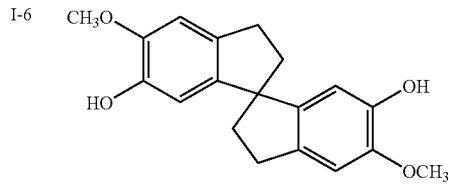

I-7
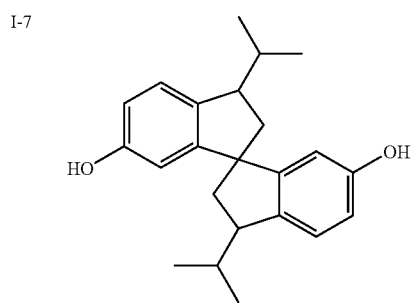

I-8
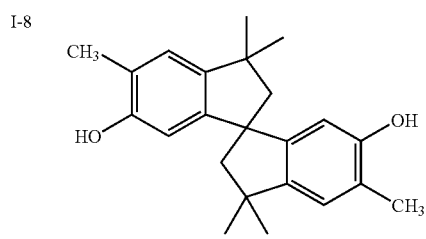

I-9
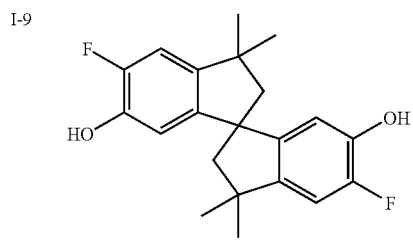

I-10
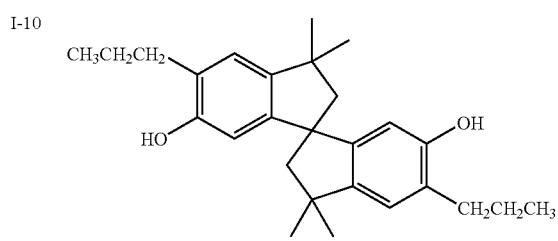

I-11
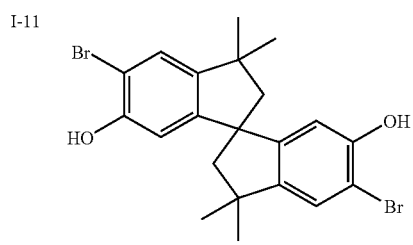

-continued

I-12
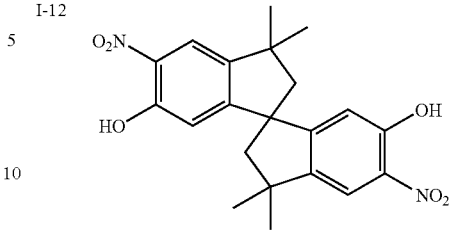

I-13
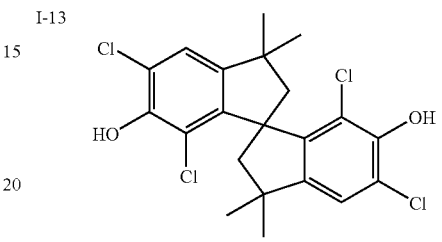

The racemic 1,1'-spirobiindane-6,6'-diol is then suitably reacted with a chiral nonracemic component to form a mixture of diastereomeric diesters, that differ only in the configuration of the spiro-fused, stereogenic center. Suitable esters are described by Structure 3, wherein all of the substituents, save $R_E$, are described as in Structure 2. In Structure 3, the two $R_E$ groups are the same. Also in structure 3, the integer m is the same and varies from 0 to 1. When m=1, the esters are carbonates.

Structure 3

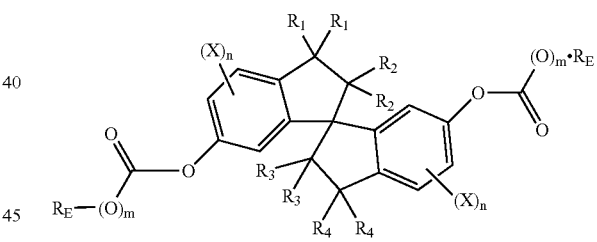

Suitable $R_E$ substituents are chiral, substantially enantiomerically pure groups. These groups may be any suitable alkyl, cycloalkyl, alkaryl, aryl either substituted or unsubstituted. When the m=0 the esters are derived from a carboxylic acids; suitable acids include (+)-camphorcarboxylic acid, (−)-camphorcarboxylic acid, podocarpic acid, (+)-cis-2-benzamidocyclohexanecarboxylic acid, dihydroabietic acid, abietic acid, (+)-camphoric acid, and (−)-camphanic acid. Preferably, the —O—$R_E$ (i.e., m=1) groups are cycloalkyl to include those derived from the conjugate bases of enantiomerically enriched menthol, fenchol, neomenthol, isomenthol, 8-phenylmenthol, borneol, trans-2-phenylcyclohexan-1-ol, isopinocampheol, isoborneol, endo-2-norborneol, dihydrocarveol, isopulegol, trans-2-tert-butylcyclohexan-1-ol, cholesterol, exo-6-hydroxytropinone trans-pinocarveol. Most suitably, the groups —O—$R_E$ (i.e., m=1) are either one or the other enantiomer of menthol, generally designated either (+)-menthyl or (−)-menthyl:

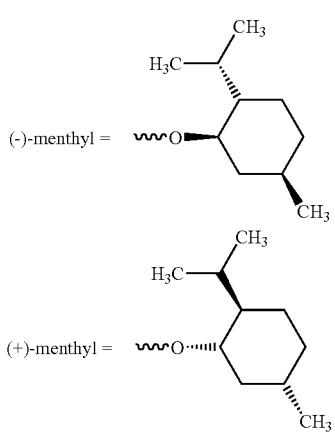

The requisite diastereomer mixtures are prepared via condensation of the racemic 1,1'-spirobiindane-6,6'-diol directly with the nonracemic chiral acid component or with a suitably activated acid component usually in an organic solvent. Such activated acid components include carboxylic acid chlorides, carboxylic acid bromides, chloroformates, carboxylic acid anhydrides, mixed carboxylic acid-sulfonic acid anhydrides, bromoformates, mixed carbonic acid-sulfonic acid anhydrides.

Direct condensations of racemic 1,1'-spirobiindane-6,6'-diol derivatives with nonracemic chiral acids can be induced via strong acids or using condensing agents. Strong acids may include minerals acids such as sulfuric acid, phosphoric acid, hydrochloric acid or organic acids such as methanesulfonic acid, trifluoromethanesulfonic acid, trifluoroacetic acid, toluenesulfonic acid, or protic acids of similar acid strength. Condensing agents may include dicyclohexylcarbodiimide, diisopropylcarbodiimide, diethyl azodicarboxylate/triphenylphosphine, diisopropyl azodicarboxylate/triphenylphosphine, and similar reagents.

Alternatively, the racemic 1,1'-spirobiindane-6,6'-diol derivatives may be converted to their corresponding bis-chloroformate, then condensed with suitable nonracemic alcohols under basic conditions to provide the desired mixture of diastereomeric diesters. Typically such bis-chloroformates may be formed from the 1,1'-spirobiindane-6,6'-diol derivatives using phosgene, or a phosgene equivalent such as trichloromethyl chloroformate (diphosgene) or bis-trichloromethyl carbonate (triphosgene), under neutral, acidic or basic conditions. The so produced racemic bis-chloroformates they may be reacted with suitable nonracemic alcohols, under basic conditions, to provide the desired mixture of diastereomeric bis-carbonates.

The procedures employed to prepare the mixture of diastereomeric diesters outlined above most usually are performed in an organic solvent or solvent mixture. Conveniently, on a laboratory-sized scale, these reactions are often run in chlorocarbon solvents, such as methylene chloride. For larger scale reactions, perhaps in a manufacturing environment, a variety of alternative solvent might readily be substituted. Typical alternative solvents include tetrahydrofuran (THF), dioxane, isopropyl ether (IPE), 1,2-dimethoxyethane (DME), ethyl acetate, propyl acetate, butyl acetate, acetonitrile, propionitrile, butyronitrile, toluene, xylenes, heptanes, N,N-dimethylformamide (DMF), N,N-dimethylacetamide (DMA), N-methylpyrrolidone (NMP), pyridine, or mixtures of such solvents.

Bases useful in the reactions of the invention include organic bases such as triethylamine, pyridine, diisopropylethylamine, 1,1,3,3-tetramethylguanadine, 1,8-diazabicyclo[5.4.0]undec-7-ene (DBU), dicyclohexylamine, and inorganic bases such as sodium bicarbonate, potassium bicarbonate, sodium carbonate, potassium carbonate, potassium phosphate, cesium carbonate, sodium acetate.

The suitably prepared mixture of diastereomeric diesters then can be separated via one of a variety of techniques known to those practiced in the art. These methods include trituration, in this case defined as stirring the material of interest with a designated organic liquid so as to induce crystallization, dissolve impurities, or allow break-up of a crystalline mass, fractional crystallization, recrystallization, achiral chromatography, high performance (or pressure) liquid chromatography (HPLC), flash chromatography. Preferably, the separation of the diastereomeric esters proceeds via trituration of the mixture with a suitable organic solvent to induce crystallization of one diastereomeric diester, followed by filtration of the solid and drying of the crystallized diastereomeric diester.

Finally, the chiral ester groups pendant on the core of the nonracemic 1,1'-spirobiindane-6,6'-diol diastereomeric diester are removed to provide the desired nonracemic 1,1'-spirobiindane-6,6'-diol enantiomers. Many methods for such ester removal are known to those practiced in the art. Of particular note are hydrolyses under strongly acid or basic aqueous conditions, transesterification usually employing acidic reagents, nucleophilic displacements, ester reductions, and similar methods. Hydrolytic conditions usually entail reaction of the ester with bases, (for example, lithium hydroxide, sodium hydroxide, potassium hydroxide or cesium hydroxide) or mineral acid (for example, sulfuric acid, phosphoric acid, hydrochloric acid) in water or mixed water/solvent reaction media. Suitable solvents include methanol, ethanol, 2-propanol, 1-propanol, THF, DMF, DMA, NMP, DME, ethylene glycol or mixtures of these solvents. Transesterifications, in this case, would usually involve reaction of the bis-ester with an excess of alcohol under acidic conditions, such that a nonracemic 1,1'-spirobiindane-6,6'-diol bis-ester would transfer its acid components to the hydroxylic solvent producing a new chiral esters and the nonracemic 1,1'-spirobiindane-6,6'-diol derivative. Suitable hydroxylic solvents include methanol, ethanol, 2-propanol, 1-propanol, ethylene glycol. Further, a suitable co-solvent may be added to improve reactant solubility.

Several examples of the invention are presented herein as demonstration of the invented and are not meant to be limiting.

EXAMPLES

Example 1

Step 1: Preparation of Racemic Chiral
1,1'-spirobiindane-6,6'-diol Derivative (±)-I–1

The synthesis of representative diol derivative compounds used in the invention, as shown in Scheme 1, begins with preparation of racemic (±)-I-1, followed by chiral resolution of this enantiomeric mixture to provide (+)-I-1. The preparation of racemic 3,3,3',3'-tetramethyl-1,1'-spirobiindan-6,6'-diol employed a minor variant of the method described by Faler and Lynch, EP264026A1. This synthetic route and its subsequent partial enantiomeric resolution are outlined in Scheme 1.

A mixture of bis-phenol A (Int-1; CAS 80-05-7; 100 g, 0.438 mole) and methanesulfonic acid (5 mL) was heated at 135° C. for three hours then cautiously poured into 550 mL water with stirring. After stirring a short while the liquid was decanted and the remaining solid diluted with 350 mL water and the stirring continued. This procedure was repeated twice further to provide a semi-solid mass. The damped solid was heated to reflux with 150 mL methylene chloride for one hour then chilled. The solid was collected, washed with minimal cold methylene chloride and ligroin to provide (±)-I-1 as a white solid 29.1 g (65%). This material proved chromatically homogenous and displayed spectral characteristics consistent with its assigned structure.

Step 2: Preparation of Diastereomeric Diester Mixture:

A solution of (±)-I-1 (12.3 g; 40 mmol), triethylamine (TEA; 20 mL, 144 mmol), and 4-dimethylaminopyridine (DMAP; 1 g, 8 mmol) in 200 mL methylene chloride was treated over circa ten minutes with a solution of (−)-menthyl chloroformate (i.e. the chloroformate derived from (−)-menthol; CAS 14602-86-9; 18 mL, 84 mmol) in 5 mL methylene chloride. The resulting mixture stirred at ambient temperature for three hours then was washed with dilute hydrochloric acid, dried with sodium sulfate, filtered and concentrated in vacuo. The glassy residue contained an equimolar mixture of the diastereomeric diesters Int-2 and Int-3 as assessed by proton NMR spectroscopy.

Step 3: Separation of Diastereomeric Diester

The glassy residue, containing an equimolar mixture of the diastereomeric diesters Int-2 and Int-3 as assessed by proton NMR spectroscopy, was dissolved in 150 mL heptanes. Shortly, crystallization initiated and the slurry stirred at ambient temperature for twenty hours. The slurry was chilled in an ice water bath then filtered; the solids washed with minimal cold heptanes and low-boiling ligroin to provide Int-2 as a colorless solid, 9.46 g (35%; 70% based on single diastereomeric diester). This material proved chromatically homogenous and displayed spectral characteristics consistent with its assigned structure. High field NMR detected none of the alternative diastereomeric diester, Int-3.

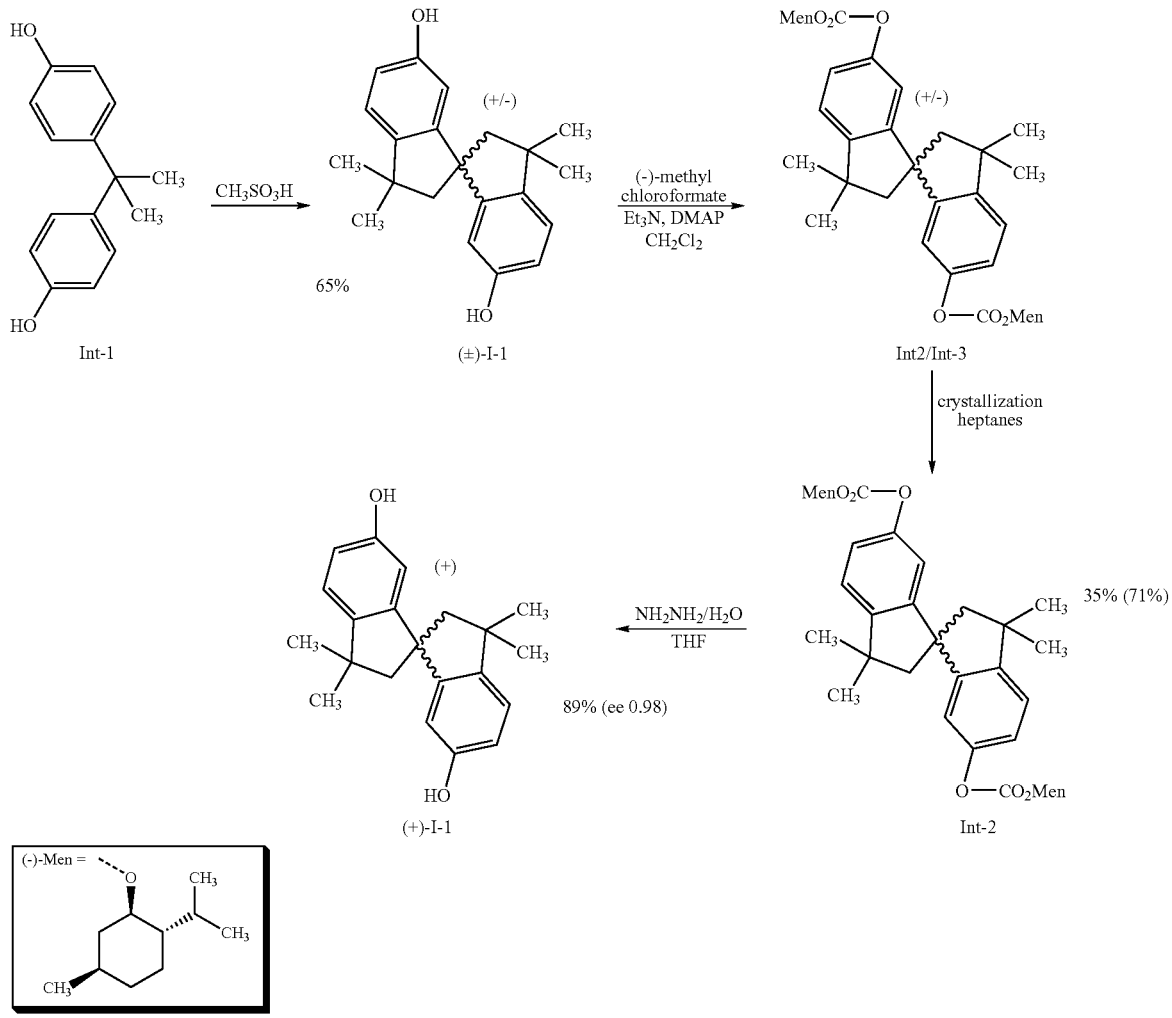

Scheme 1

Step 4: Removal of Ester Groups

A solution of Int-2 (9.00 g, 13.4 mmol) and hydrazine monohydrate (4.6 mL, 95 mmol) in 85 mL tetrahydrofuran (THF) was heated at reflux for three hours then portioned between dilute hydrochloric acid and ethyl acetate. The organic layer wash dried with sodium sulfate, filtered and concentrated in vacuo to provide an oil.

Step 5: Optional Further Purification of Nonracemic Chiral 1,1'-spirobiindane-6,6'-diol Derivative Two silica gel chromatographies, first eluting with mixture of methylene chloride and ethyl acetate, then secondly, eluting with mixtures of heptanes and isopropyl ether, gave a purified oil. Trituration with IPE/heptanes, followed by filtration and drying, finally yielded (+)-I-1 as a colorless solid, 3.66 g (88.6%). This material proved chromatically homogenous and displayed spectral characteristics consistent with its assigned structure. Chiral HPLC analysis indicate an % ee of >98%; Polarimetry provided $[\alpha]_D^{23}=+37.4°$ (methanol, c=0.010).

Example 2

Step 1: Preparation of Racemic Chiral 1,1'-spirobiindane-6,6'-diol Derivative and

Step 2: Preparation of Diastereomeric Diester Mixture:

A second run (1.9× the original scale) of the chiral resolution of (±)-I-1 was accomplished as in Example 1, except the crude reaction product was not chromatographed.

Step 3: Separation of Diastereomeric Diester Mixture

The reaction product was directly dissolved in 250 mL low-boiling ligroin (pentanes) and chilled in an acetone/ice (ca. −20° C.) bath to induce crystallization. After two hours the cold slurry was filtered and the solid washed with minimal pentanes. The solid diastereomeric diester Int-2 was obtained as a colorless solid in 42% (84% based on single diastereomeric diester) yield. This material proved chromatically homogenous and displayed spectral characteristics consistent with its assigned structure. Analytical HPLC indicated 99.2% diastereomeric purity.

Step 4: Removal of Ester Groups

A second run (1.6× the original scale) of the preparation of (+)-I-1 was accomplished as in Example 1, except the crude reaction product was not chromatographed, but rather triturated with isopropyl ether to provide (+)-I-1 as a colorless solid (5.46 g, 85%). This material proved chromatically homogenous and displayed spectral characteristics consistent with its assigned structure. Chiral HPLC analysis indicated 99.9% enantiomer purity.

Example 3

Step 1: Preparation of Racemic Chiral 1,1'-spirobiindane-6,6'-diol Derivative and

Step 2: Preparation of Diastereomeric Diester Mixture:

Another run (1.4× the original scale) of the chiral resolution of (±)-I-1 was accomplished as in Example 1, except (+)-menthyl chlorformate (i.e. the chloroformate derived from (+)-menthol; CAS 7635–54–3) the crude reaction product was not chromatographed.

Step 3: Separation of Diastereomeric Diester Mixture

The crude reaction product was directly dissolved in 250 mL low-boiling ligroin (pentanes) and chilled in an acetone/ice (ca. −20° C.) bath to induce crystallization. After two hours the cold slurry was filtered and the solid washed with minimal pentanes. The solid diastereomeric diester Int-4 was obtained as a colorless solid in 36% (72% based on single diastereomeric diester) yield. This material proved chromatically homogenous and displayed spectral characteristics consistent with its assigned structure. Proton NMR indicated none of the alternative diastereomeric diester.

Step 4: Removal of Ester Groups

A run of the preparation of (−)-I-1 was accomplished as for its epimer in Example 1, except the crude reaction product was not chromatographed, but rather triturated with heptanes to provide (−)-I-1 as a colorless solid (5.29 g, 89%). This material proved chromatically homogenous and displayed spectral characteristics consistent with its assigned structure. Chiral HPLC analysis indicated 99.1% enantiomer purity.

Example 4

Step 1: Preparation of Racemic Chiral 1,1'-spirobiindane-6,6'-diol Derivative (±)-Int-8

A mixture Montmorillonite K10 clay (CAS 1318-93-0; 20 g, dried ≧100° C. in vacuo) and 100 mL xylenes were refluxed under a Dean-Stark trap for twenty minutes, then 1,5-(4-methoxyphenyl)-3-pentanone (Int-6; CAS 74882-32-9, prepared via standard synthetic procedures outlined in Scheme 2; 4.00 g, 13.4 mmol) was added and the reflux continued for twenty hours. The mixture was briefly cooled and then filtered through diatomaceous earth. The solids were washed with toluene (100 mL in portions). The combined filtrates were concentrated in vacuo to provide a crude solid. This material was carefully chromatographed on silica gel, eluting with mixtures of heptanes and ethyl acetate, to provide a purified semi-solid. Trituration of this material with cold isopropyl ether then provided Int-7 as a colorless solid, 0.75 g (20%). This material proved chromatically homogenous and displayed spectral characteristics consistent with its assigned structure.

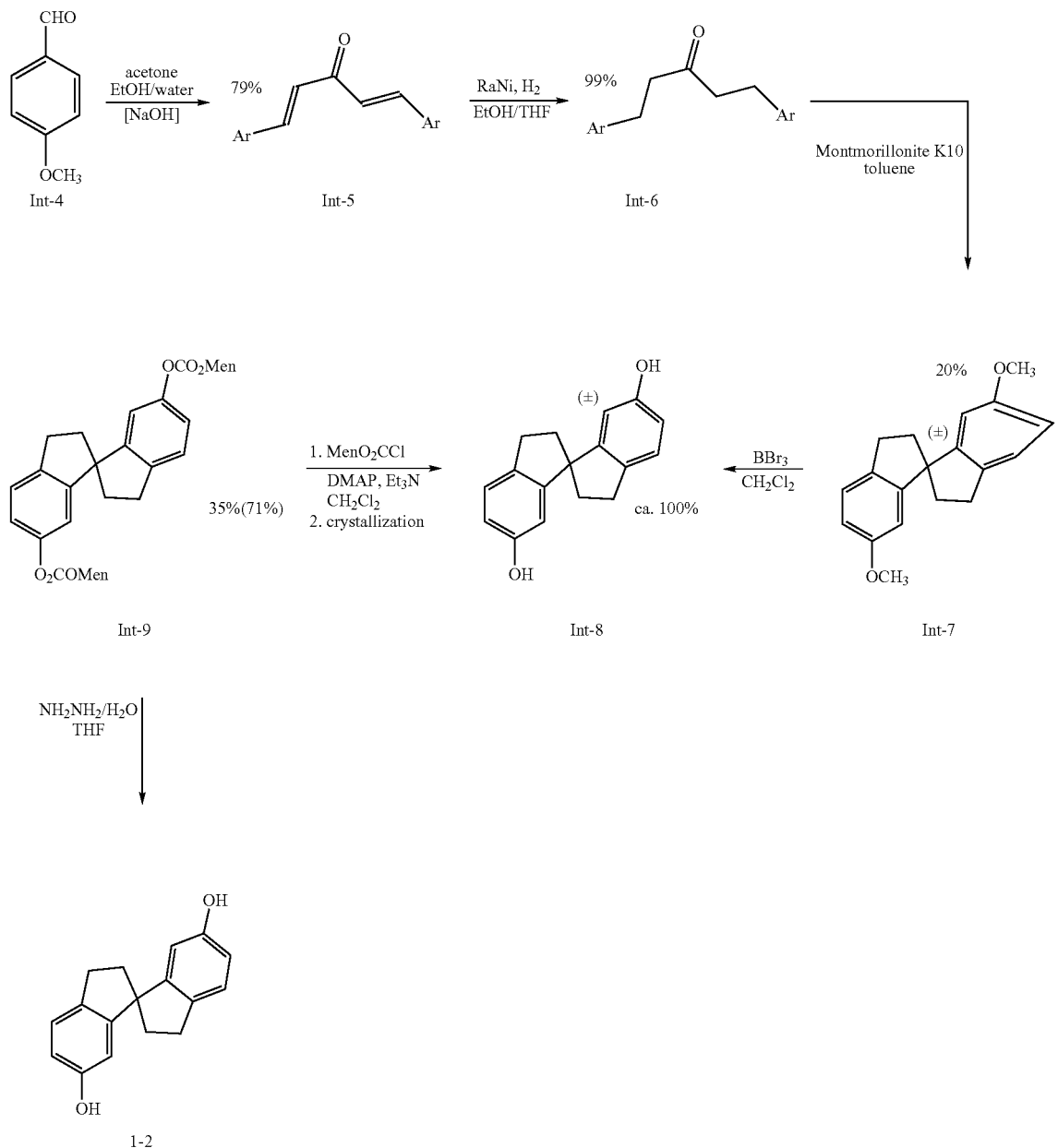

Scheme 2

A solution of Int-7 (0.56 g, 2.0 mmol) in 10 mL methylene chloride was chilled in an ice-acetone bath then treated with boron tribromide (0.45 mL, 4.8 mmol). The mixture stirred at ambient temperature for one hour then was cooled and the reaction quenched by the cautious addition of 5 mL water. The organics were separated, dried with sodium sulfate, filtered and concentrated in vacuo. The residue was treated with isopropyl ether and heptane to induce crystal formation. These solvents were removed in vacuo to provide Int-8 as a colorless solid, 0.5 g (circa 100%). This material proved chromatically homogenous and displayed spectral characteristics consistent with its assigned structure.

Step 2: Preparation of Diastereomeric Diester Mixture:

A slurry of Int-8 (0.45 g, 1.8 mmol) in 15 mL methylene chloride, at ambient temperature, was sequentially treated menthyl chloroformate (0.8 mL, 3.7 mmol), triethylamine (0.9 mL, 6.5 mmol) and DMAP (0.05 g, 0.4 mmol). The mixture was stirred at ambient temperature for one hour, and then washed with dilute hydrochloric acid. The organics were dried with sodium sulfate, filtered and concentrated in vacuo. The residue was chromatographed on silica gel, eluting with methylene chloride, top provide the expected mixture of diastereomeric diesters as a colorless oil, 1.1 g (circa 100%). NMR analysis indicated an equimolar mixture of diastereomeric diesters.

Step 3: Separation of Diastereomeric Diester Mixture

This residue was dissolved in 15 mL heptanes after which crystallization initiated. The mixture stirred at ambient temperature for thirty minutes then was filtered, to yield Int-9 as a colorless solid, 0.39 g (35%, 71% based on a single diastereomeric diester). This material proved chromatically homogenous and displayed spectral characteristics consistent with its assigned structure. Careful NMR analysis indicated the presence of a single diastereomeric diester.

Step 4: Removal of Ester Groups—Hydrazine Method

A solution of Int-9 (0.35 g, 0.57 mmol) in 7.5 mL THF was treated with hydrazine monohydrate (0.25 mL, 5.2 mmol) then heated at reflux for thirty minutes. Additional hydrazine monohydrate was added (0.15 mL, 3.1 mmol) and mix heated another hour. The mix stirred at ambient temperature overnight then was partitioned between dilute hydrochloric acid and ethyl acetate. The organic layer was dried with sodium sulfate, filtered and concentrated in vacuo to provide a glassy residue. Silica gel chromatography, eluting with mixtures of methylene chloride and ethyl acetate, gave a purified oil. This oil was dissolved ethyl acetate then washed with dilute aqueous sodium hydroxide. The aqueous layer was acidified with hydrochloric acid and extracted with ethyl acetate. The organics were dried, filtered, and concentrated to provide I-2 as a colorless oil, 0.14 g ((100%). This material proved chromatically homogenous and displayed spectral characteristics consistent with its assigned structure. The enantiomeric excess was taken to be circa 1 based upon NMR of the purified diastereomeric diester.

Step 4: Removal of Ester Groups—Alkaline Hydrolysis Method:

A mixture of Int-9 (43 mg, 0.0070 mmol) in a mixture of 5 mL methanol and 3 mL THF with sodium hydroxide (0.3 mL of a 10 Wt % aqueous solution) was refluxed for 3 h. The mixture was poured into dilute aqueous sodium hydroxide and the mixture extracted with ethyl acetate. The ethyl acetate was further extracted with portions of 10 Wt % aqueous sodium hydroxide (four times 5 mL). The aqueous portions were made acidic (pH≦2) by the addition of concentrated hydrochloric acid. Ethyl acetate extractive workup provided, after drying and concentration in vacuo, I-2 as an oil (14 mg, 78%). NMR analysis confirmed the assigned structure. Chiral HPLC analysis indicated 98.8% enantiomeric purity.

The invention has been described in detail with particular reference to certain preferred embodiments thereof, but it will be understood that variations and modifications can be effected within the spirit and scope of the invention.

The invention claimed is:

1. A method for the chemical separation of the enantiomers of 1,1'-spirobiindane-6,6'-diol derivatives comprising:
   a. providing a racemic chiral 1,1'-spirobiindane-6,6'-diol derivative;
   b. reacting a nonracemic chiral component with said racemic chiral 1,1'-spirobiindane-6,6'-diol derivative to afford a mixture of diastereomeric diesters;
   c. separating said mixture of diastereomeric diesters to provide a substantially pure individual diastereomeric diester; and
   d. chemically removing the ester groups from said substantially pure individual diastereomeric diester to provide a nonracemic chiral 1,1'-spirobiindane-6,6'-diol derivative.

2. The method of claim 1 wherein said 1,1'-spirobiindane-6,6'-diol derivative is described by Structure 2:

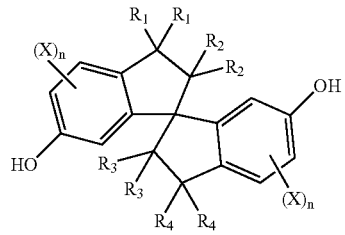

Structure 2

Wherein:
   $R_1$, $R_2$, $R_3$, and $R_4$ are independently hydrogen, or any carbon substituents;
   X independently represents any substituent group;
   n independently represents an integer 0–3: and
   wherein substituents $R_1$, $R_2$, $R_3$, $R_1$, and X may form a ring.

3. The method of claim 2 wherein $R_1$, $R_2$, $R_3$, and $R_4$ are hydrogen or a lower alkyl group.

4. The method of claim 2 wherein $R_1$ and $R_4$ are hydrogen or methyl, $R_2$ and $R_3$ are hydrogen, and n=1.

5. The method of claim 1 wherein said 1,1'-spirobiindane-6,6'-diol derivative is described by Structure I-1:

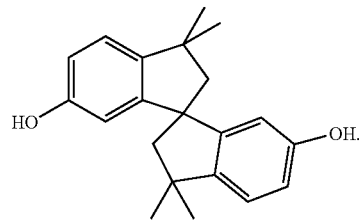

I-1

6. The method of claim 1 wherein said 1,1'-spirobiindane-6,6'-diol derivative is described by Structure I-2:

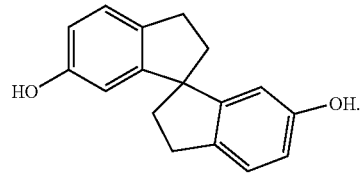

I-2

7. The method of claim 1 wherein said reacting is via condensation.

8. The method of claim 1 wherein said chiral nonracemic component is an acid component.

9. The method of claim 8 wherein said acid component is a member selected from the (+)-camphorcarboxylic acid, (−)-camphorcarboxylic acid, podocarpic acid, (+)-cis-2-benzamidocyclohexanecarboxylic acid, dihydroabietic acid, abietic acid, (+)-camphoric acid, (−)-camphanic acid.

10. The method of claim 8 wherein said acid component is (+)-camphorcarboxylic acid or (−)-camphorcarboxylic acid.

11. The method of claim 8 wherein said acid component is acid chloride.

12. The method of claim 1 wherein said chiral nonracemic component is a condensing agent.

13. The method of claim 12 wherein said condensing agent is a member selected from the group consisting of dicyclohexylcarbodiimide, diisopropylcarbodiimide, diethyl azodicarboxylate/triphenylphosphine, and diisopropyl azodicarboxylate/triphenylphosphine.

14. The method of claim 12 wherein said condensing agent is diisopropylcarbodiimide.

15. The method of claim 1 wherein said chiral nonracemic component is an activated acid component.

16. The method of claim 15 wherein said activated acid component is in an organic solvent or mixtures thereof.

17. The method of claim 16 wherein said organic solvents comprise at least one member selected from the group consisting of methylene chloride, tetrahydrofuran (THF), dioxane, isopropyl ether (IPE), 1,2-dimethoxyethane (DME), ethyl acetate, propyl acetate, butyl acetate, acetonitrile, propionitrde, butyronitrile, toluene, xylenes, heptanes, N,N-dimethylformamide (DMF), N,N-dimethylacetamide (DMA), N-methylpyrrolidone (NMP), and pyridine.

18. The method of claim 16 wherein said organic solvent is methylene chloride.

19. The method of claim 15 wherein said activated acid component comprises at least one member selected from the group consisting of carboxylic acid chlorides, carboxylic acid bromides, chloroformates, carboxylic acid anhydrides, mixed carboxylic acid-sulfonic acid anhydrides, bromoformates, and mixed carbonic acid-sulfonic acid anhydrides.

20. The method of claim 15 wherein said activated acid component is a chloroformate.

21. The method of claim 1 wherein said reacting is via conversion of said racemic 1,1'-spirobiindane-6,6'-diol derivatives to their corresponding bis-chloroformate, followed by condensation with nonracemic alcohols under basic conditions.

22. The method of claim 21 wherein said conversion is accomplished through reaction of said racemic 1,1'-spirobiindane-6,6'-diol derivatives with phosgene, trichloromethyl chloroformate (diphosgene), or bis-trichloromethyl carbonate (triphosgene).

23. The method of claim 21 wherein said diastereomeric diesters are diastereomeric bis-carbonates.

24. The method of claim 21 wherein said basic conditions are produced through the use of at least one member of the group consisting of triethylamine, pyridine, diisopropylethylamine, 1,1,3,3-tetramethylguanadine, 1,8-diazabicyclo[5.4.0]undec-7-ene (DBU), dicyclohexylamine, sodium bicarbonate, potassium bicarbonate, sodium carbonate, potassium carbonate, potassium phosphate, cesium carbonate, and sodium acetate.

25. The method of claim 21 wherein said basic conditions are produced through the use of potassium carbonate.

26. The method of claim 21 wherein said basic conditions are produced through the use of triethylamine.

27. The method of claim 1 wherein said diastereomeric diesters are represented by Structure 3:

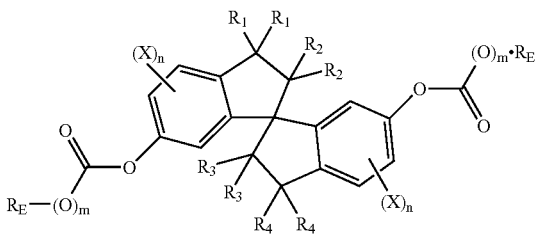

Structure 3 wherein:
$R_1$, $R_2$, $R_3$, and $R_4$ are independently hydrogen, or any carbon substituents;
X independently represents any substituent group;
n independently represents an integer 0–3;
wherein substituents $R_1$, $R_2$, $R_3$, $R_4$, and X may form a ring; $R_E$ represents chiral, substantially enantiomerically pure groups; and
m is from 0 to 1.

28. The method of claim 27 wherein m=1 and the esters are carbonates.

29. The method of claim 27 wherein $R_E$ represents substituted or unsubstituted alkyl, cycloalkyl, alkaryl, or aryl groups.

30. The method of claim 27 wherein m=1 and —O—$R_E$ groups are cycloalkyl groups selected from the group consisting of conjugate bases of enantiomerically enriched menthol, fenchol, neomenthol, isomenthol, 8-phenylmenthol, borneol, trans-2-phenylcyclohexan-1-ol, isopinocampheol, isoborneol, endo-2-norborneol, dihydrocarveol, isopulegol, trans-2-tert-butylcyclohexan-1-ol, cholesterol, and exo-6-hydroxytropinone trans-pinocarveol.

31. The method of claim 27 wherein m=1 and —O—$R_E$ groups are an enantiomer of menthol, designated (+)-menthyl or (−)-menthyl:

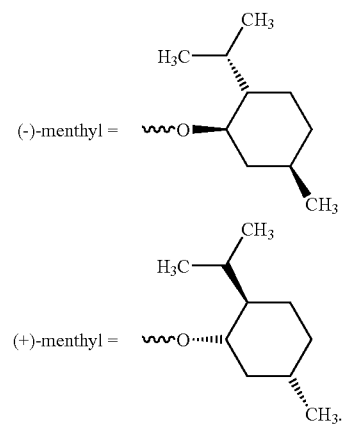

32. The method of claim 1 wherein said separating is accomplished by trituration, fractional crystallization, recrystallization, achiral chromatography, high performance (or pressure) liquid chromatography (HPLC), or flash chromatography.

33. The method of claim 1 wherein said separating is by trituration.

34. The method of claim 33 wherein said trituration is trituration with a suitable organic solvent to induce crystallization of one diastereomeric diester, followed by filtration and drying of the crystallized diastereomeric diester.

35. The method of claim 1 wherein said removing comprises hydrolyses, transesterification, nucleophilic displacements, and ester reductions.

36. The method of claim 1 wherein said removing is via hydrolysis.

37. The method of claim 36 wherein said hydrolysis comprises reaction of said diastereometric esters with base or mineral acid.

38. The method of claim 37 wherein said base comprises at least one member selected from the group consisting of lithium hydroxide, sodium hydroxide, potassium hydroxide and cesium hydroxide.

39. The method of claim 37 wherein said base comprises sodium hydroxide.

40. The method of claim 37 wherein said mineral acid is sulfuric acid, phosphoric acid, or hydrochloric acid.

41. The method of claim 37 further comprising solvent.

42. The method of claim 41 wherein said solvent comprises water.

43. The method of claim 41 wherein said solvent comprises at least one member selected from the group consisting of methanol, ethanol, 2-propanol, 1-propanol, THF, DMF, DMA, NMP, DME), ethylene glycol and water.

44. The method of claim 41 wherein said solvent comprises ethanol.

45. The method of claim 32 wherein transesterifications comprises reaction of said diasteomeric ester with an excess of alcohol under acidic conditions.

46. The method of claim 45 further comprising at least one hydroxylic solvent selected from the group consisting of methanol, ethanol, 2-propanol, 1-propanol, and ethylene glycol.

* * * * *